(12) United States Patent
Akazawa

(10) Patent No.: US 6,770,309 B2
(45) Date of Patent: *Aug. 3, 2004

(54) METHOD OF PROCESSING SOYBEAN BY USE OF AN ENZYME, PROCESSED SOYBEAN OBTAINED BY THE SAME METHOD, AND FOOD CONTAINING THE PROCESSED SOYBEAN

(75) Inventor: Toru Akazawa, Takarazuka (JP)

(73) Assignee: Yugengaisha Chima, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/177,923

(22) Filed: Jun. 24, 2002

(65) Prior Publication Data

US 2002/0197350 A1 Dec. 26, 2002

Related U.S. Application Data

(63) Continuation of application No. 09/508,532, filed as application No. PCT/JP99/04258 on Aug. 6, 1999, now Pat. No. 6,410,064.

(51) Int. Cl.[7] .................................................. A23L 1/20
(52) U.S. Cl. .......................................... 426/46; 426/634
(58) Field of Search ............................. 426/46, 50, 51, 426/52, 555, 549, 574, 565, 653, 634

(56) References Cited

U.S. PATENT DOCUMENTS

| 4,119,733 A | 10/1978 | Hsieh et al. |
| 4,882,180 A | 11/1989 | Takao et al. |

FOREIGN PATENT DOCUMENTS

| GB | 2119218 A | 11/1983 |
| JP | 37-18572 | 12/1937 |
| JP | 42-22169 | 10/1942 |
| JP | 49-19056 | 2/1974 |
| JP | 53-9339 | 1/1978 |
| JP | 53-145957 | 12/1978 |
| JP | 54-113458 | 9/1979 |
| JP | 55-153573 | 11/1980 |
| JP | 61012261 A | 1/1986 |
| JP | 61115458 A | 6/1986 |
| JP | 61-219347 | 9/1986 |
| JP | 01153056 A | 6/1989 |
| JP | 01257440 A | 10/1989 |
| JP | 02057154 A | 2/1990 |
| JP | 03127958 A | 5/1991 |
| JP | 6105661 | 4/1994 |
| JP | 8-89197 | 4/1996 |
| JP | 09070274 A | 3/1997 |
| JP | 9094068 | 4/1997 |

OTHER PUBLICATIONS

Akira Kaji, Isamu Fujikawa, Shojiro Iwahara and Masayuki Sato, Journal of Agricultural Chemistry, 46th vol., No. 10, published on 1972, pp. 509–516, Pectolytic Enzymes with the Macerating Activity Produced by Bacillus sp. F–11, Abstract.

Shigetaka Ishii, Satoshi Kawamura and Tamotsu Yokotsuka, Journal of Agricultural Chemistry, 44th vol., No. 7, published on 1970, pp. 306–311, "Studies on the Enzymatic Degradation of Plant Tissue Part IV. Macerating Activity of *Aspergillus sojae* No. 48", Abstract.

Zymurgy, published on Apr. 10, 1982, Kodansha Ltd., pp. 160–162, Abstract.

Foods and Science, 32nd vol., No. 5, published on Apr. 10, 1990, pp. 96–107, Abstract.

Soybeans–Healthy Protein Born from the Field, published on Jul. 1984, Kagawa Nutrition University Publishing Division, pp. 107–109, Abstract.

About Technical Problems of Bean–Paste Processed Foods and Raw Material for Bean Paste, published on Sep. 1968, pp. 14–16, Abstract.

Food Engineering and Enzymes, published on Sep. 25, 1985, pp. 73–75, Abstract.

"Production of Constitutive, Thermostable, Hyper Active Exo–Pectinase From Bacillus GK–8," Biotechnology Letters, vol. 18, No. 12, Dec. 1996, pp. 1435–1438.

*Primary Examiner*—Keith Hendricks
(74) *Attorney, Agent, or Firm*—Rader, Fishman & Grauer PLLC

(57) ABSTRACT

A method of processing soybean by use of an enzyme is provided. After the soybean is soaked in water, it is steamed. The steamed soybean is cooled, and then water and a pectinase produced by microorganisms of the genus Bacillus are added to the soybean to prepare a first mixture. The first mixture is held for a predetermined time period while being agitated to accomplish an enzyme treatment, so that a slurry is obtained, in which single cells of the soybean are dispersed. After the enzyme treatment, the pectinase is inactivated. Next, the slurry is mixed with a powder obtained by processing a pulse other than the soybean to obtain a second mixture. The second mixture is dried by flash drying or spray drying operation to obtain a processed soybean powder. By omitting the steps performed after the step of inactivating the pectinase, it is possible to obtain a processed soybean liquid, in which the single cells of the soybean are dispersed.

9 Claims, 2 Drawing Sheets

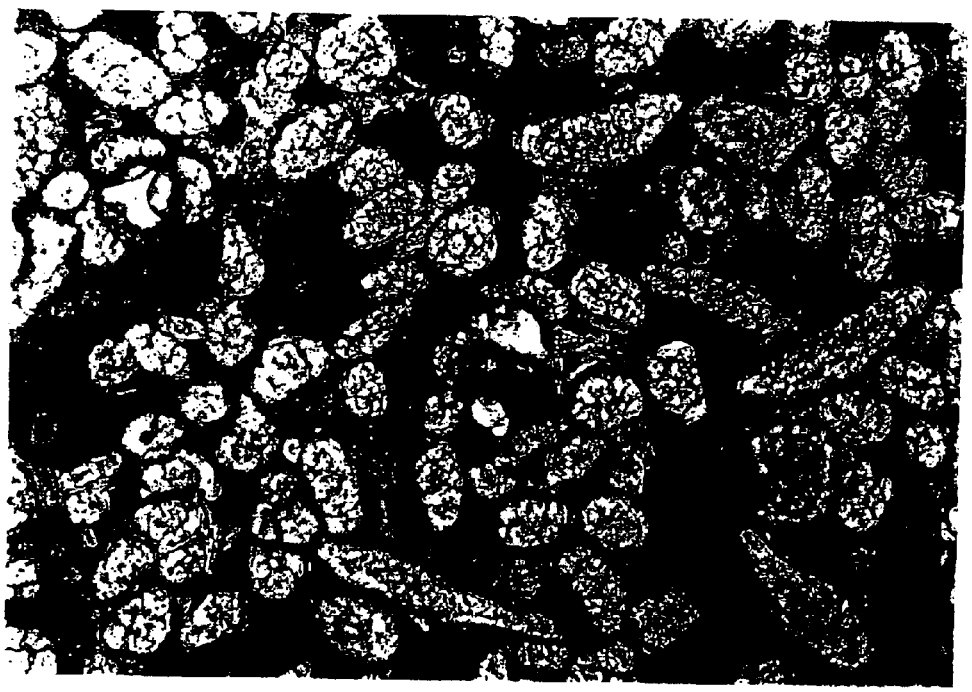
FIG. 1 100 μm
50 μm
FIG. 2

FIG. 3  $\overline{100 \mu m}$

METHOD OF PROCESSING SOYBEAN BY USE OF AN ENZYME, PROCESSED SOYBEAN OBTAINED BY THE SAME METHOD, AND FOOD CONTAINING THE PROCESSED SOYBEAN

This is a continuation of Ser. No. 09/508,532, now U.S. Pat. No. 6,410,064, which is the National Stage of PCT/JP99/04258, filed Aug. 6, 1999.

TECHNICAL FIELD

The present invention relates to a method of processing soybean by use of an enzyme, and particularly a method of processing soybean, which comprises the step of efficiently separating soybean cells from each other by use of a pectinase produced by microorganisms of the genus Bacillus. In addition, the present invention relates to a processed soybean obtained by the same method, and a food containing the processed soybean.

BACKGROUND ART

Soybean, which has been known as the "miracle crop", is a nutritious food material containing abundant vitamins and well-balanced protein, carbohydrate and lipid components. In particular, the quality of the soybean protein is so excellent that it is often called "the meat of the field".

Soybean also contains natural isoflavone. In recent years, isoflavone has gained public attention because it produces a similar action to female hormone, and is useful to reduce dissolution of calcium from the human body and to prevent rapidly increasing cases of osteoporosis. In addition, it is said that isoflavone has an effect of preventing menopausal disorder and cancer and improving their symptoms. Furthermore, the soybean contains such constituents as saponin, peptide and lecithin. It is said that these constituents are useful to prevent diseases attributable to habits in life (diseases common in adults).

However, since the soybean has a hard tissue, its digestion-absorption coefficient for the human body is low in case of eating boiled or roasted soybean. Therefore, a processed soybean is produced by mashing the soybean after heating to thereby improve the digestion-absorption coefficient. Well-known processed soybean foods available today include, for example, soybean milk obtained by mashing soybean, heating the mashed soybean and then performing a filtering operation, and tofu obtained by adding a protein coagulant to the soybean milk to coagulate nutritious constituents of the soybean milk together with the protein. In addition, soybean oil can be obtained by extracting oil and fat from the soybean.

Thus, improving the digestion-absorption coefficient by the processed soybean foods has made it possible to eat soybean while enjoying various tastes and feelings of eating. However, water-soluble proteins and emulsified oil and fat of soybean are mainly used to obtain the soybean milk and tofu. The residue of soybean is thrown away as okara (strained draff weighing about 30 to 50% of raw soybean). In addition, only 20% of soybean is used as the soybean oil, and the remaining soybean cake is used almost entirely as animal feeds and fertilizers. In the future, it is predicted that food shortages become more serious. Therefore, developing a method of processing the whole of soybean as food material will be a countermeasure for the predicted food shortages.

In the past, efforts have been made to use a soybean powder obtained by mechanically pulverizing soybean or soybean cake. However, since soybean cells are destroyed during the pulverizing operation, the soybean powder has a smell characteristic to soybean. Due to this smell, even when the soybean powder is used together with other foods, original tastes of the foods are deteriorated. This limits the scope of its application and the amounts added as a food ingredient. Although soybean proteins extracted from soybean cake are often used for processed foods, the application is limited due to the soybean smell, too. Consequently, soybean cake is used almost entirely as animal feeds and fertilizers under the present circumstances.

For example, Japanese Patent Early Publication [KOKAI] No. 61-219347 discloses a decomposed product of soybean and its production method. This method comprises the steps of pulverizing soybean, adding water to the pulverized soybean to obtain a slurry, heating the slurry at a temperature from 60° C. to 100° C. for a time period of 5 to 180 minutes, homogenizing the heated slurry under high pressure (100 to 800 kg/cm$^2$), and hydrolyzing a resultant homogenate with a neutral protease (enzyme capable of breaking a peptide bond between protein and peptide) produced by the *Bacillus subtilis*. After a resultant hydrolyzate is heated and maintained for a required time period to inactivate the enzyme action, it is dried by way of spray drying to obtain the decomposed product of the soybean.

According to this method, the entire constituents of soybean can be used, and the digestion-absorption coefficient for the human body can be improved. However, since the soybean cells are destroyed during the pulverizing step and the homogenizing treatment performed under the high pressure, there is a problem that the characteristic soybean smell originating from intracellular constituents remains in the decomposed product.

On the other hand, Japanese Patent Early Publication [KOKAI] No. 8-89197 discloses a method of producing a processed soybean food such as soybean milk. This method comprises the steps of adding water to soybean, keeping the soybean at room temperature for a required time period, adding a protopectinase to the soybean to obtain a mixture, holding this mixture at room temperature (for example, 28° C.) for a long time period (for example, 8 hours) while agitating the mixture to achieve an enzyme treatment, and then filtrating the soybean from the mixture to obtain the soybean milk. It is also described that a mixture of protopectinase and pectinesterase, pectin-polygalacturonase or polygalacturonase may be used for the enzyme treatment.

According to this method, it is possible to separate soybean cells from each other without destroying the soybean cells. Each of the separated soybean cells maintains a state of enveloping nutritious constituents such as proteins and fat in the cell wall. Therefore, the problem of the characteristic soybean smell originating from the intracellular constituents can be solved. However, the enzyme treatment for separating the soybean cells from each other has not necessarily been sufficient for reasons stated below. Since the enzyme treatment using the aforementioned enzyme is performed at room temperature, there is a problem that various germs easily propagate to induce the occurrence of smell and bubbles by fermentation. In addition, since the time required for the enzyme treatment is extremely long, there is a problem that the production efficiency is too low for industrial applications.

Japanese Patent Publication No. 42-22169 discloses a method of producing an easily dispersible powder food from beans. This method comprises the steps of adding a protopectinase produced by microorganisms of the genus Rhizopus to soybean previously soaked in water to perform an enzyme treatment, separating the treated soybean by filtration, and drying the separated soybean by a freeze drying method to obtain the powder food. It is also described that a protopectinase produced by microorganisms of the genus Aspergillus or Penicillium may be used for the enzyme treatment.

However, this method has substantially the same problems that were described above with reference to Japanese Patent Early Publication [KOKAI] No. 8-89197.

DISCLOSURE OF THE INVENTION

In consideration of the above problems, a primary object of the present invention is to provide a method of processing soybean by use of an enzyme, which is capable of efficiently producing a processed soybean food having substantially no smell characteristic to the soybean and an improved digestion-absorption coefficient for the human body by using the entire constituents of the soybean. The processing method of the present invention is characterized by the following steps. That is, the soybean is soaked in water, and then heated in the presence of water. After the heated soybean is cooled, an enzyme treatment is performed by adding water and a pectinase produced by microorganisms of the genus Bacillus to the soybean to obtain a first mixture, and holding the first mixture for a predetermined time period while agitating the first mixture to thereby obtain a slurry, in which single cells of the soybean are dispersed. After the enzyme treatment, the pectinase is inactivated. Next, a second mixture is prepared by mixing the slurry with a powder obtained by processing a pulse other than the soybean. The second mixture is dried by a flash drying or spray drying method to obtain a processed soybean powder.

The above-described method of the present invention presents the following advantages.

1. By use of the pectinase produced by the microorganisms of the genus Bacillus, the soybean cells can be separated from each other in a very short time as compared to the conventional case. In addition, the separated soybean cells are characterized in that damages to cell membranes and cell walls are small, and protein bodies and lipid bodies are stably maintained in the interior of each of the separated soybean cells. Thus, it is possible to provide the separated soybean cells of high quality.
2. Since the enzyme treatment can be performed at a high temperature of about 60° C. by use of the pectinase produced by the microorganisms of the genus Bacillus, it is possible to prevent the propagation of various germs as compared to the enzyme treatment using an enzyme produced by microorganisms of the genus Rhizopus or the like. Therefore, the enzyme treatment is advantageous in obtaining fresh soybean single cells. Additionally, since the pectinase shows a high enzyme activity in a range from neutrality to low alkalinity, i.e., a pH range of 7 to 8, it is possible to perform the enzyme treatment without using a pH-controlling agent.
3. By combination of the step of preparing the second mixture by mixing the slurry with the powder obtained by processing the pulse other than the soybean and the step of drying the second mixture by the flash drying or spray drying method, it is possible to produce the processed soybean powder having substantially no smell characteristic to the soybean and uniform quality without giving damages to the separated soybean cells.

Another object of the present invention is to provide a method of processing soybean by use of an enzyme, which is characterized by the following steps. That is, the soybean is soaked in water, and then heated in the presence of water. After the heated soybean is cooled, an enzyme treatment is performed by adding water and a pectinase produced by microorganisms of the genus Bacillus to the soybean to obtain a mixture, and holding the mixture for a predetermined time period while agitating the mixture. After the enzyme treatment, the pectinase is inactivated to thereby obtain a processed soybean liquid, in which single cells of the soybean are dispersed. Therefore, the present invention is useful for providing the processed soybean liquid as well as the processed soybean powder.

A further object of the present invention is to provide a processed food produced by adding the processed soybean powder or the processed soybean liquid obtained by the present method to a food ingredient.

These and other objects and advantages will become apparent from the following detailed description of the preferred embodiments and examples of the invention.

BRIEF DECRIPTION OF THE DRAWINGS

FIG. 1 is an optical microscope photograph (taken at a low magnification) of a processed soybean powder obtained by a method of processing whole soybean according to the present invention;

FIG. 2 is an optical microscope photograph (taken at a high magnification) of the processed soybean powder obtained by the method of processing the whole soybean according to the present invention; and FIG. 3 is an optical microscope photograph of a bread made by use of the processed soybean powder of the present invention.

DETAILED DESCRIPTION OF THE INVENTION

Following is a detailed description of a method of processing soybean by use of an enzyme according to the present invention.

First, a predetermined amount of soybean is washed with water, and then soaked in water. This soaking step is performed to supply a sufficient amount of water into individual cells of the soybean, so that a later enzyme treatment becomes easier to perform. Although the soaking time is not particularly limited, it is preferred to soak the soybean in water for a time period of 12 to 15 hours. If necessary, water containing a small amount of pectinase used in the enzyme treatment to be described later may be used in this soaking step.

Subsequently, the soybean is heated in the presence of water. This step is performed to inactivate an action of lipoxigenase contained in soybean, and improve the digestion-absorption coefficient for the human body by thermal denaturation of soybean protein. In addition, this step softens the intercellular substance of soybean, so that the later enzyme treatment becomes easier to perform. To efficiently achieve these purposes, it is particularly preferred to steam the soybean. For example, it is preferred to steam the soybean at 120° C. for 10 minutes by use of a pressure cooker.

After the steamed soybean has been cooled down to a specified temperature, water and the pectinase produced by microorganisms of the genus Bacillus are added to the soybean to obtain a first mixture. It is preferred that the steamed soybean is cooled to a temperature of performing the enzyme treatment, for example, 60° C. From the viewpoint of zero-emission process, i.e., for avoiding the occurrence of waste as far as possible during the method of processing the soybean of the present invention, and for making effective use of a small amount of soybean constituents (primarily proteins) oozed out from the soybean in the soaking step, it is preferred to add the water used in the soaking step to the soybean. It is also preferred that the amount of added water be substantially equal to the weight of the soybean measured after the steaming. On the other hand, it is preferable that the amount of pectinase to be added fall within a range of 0.05 to 0.2 wt % of the weight of the soybean measured before the soaking step, and it is particularly preferable that the amount of pectinase to be added be approximately 0.1 wt % of the weight of the soybean.

The first mixture is held, for example, at 60° C. for 30 minutes while being agitated to achieve the enzyme treatment. From preliminary experiments, it has been confirmed that a maximum enzyme activity of the pectinase produced by microorganisms of the genus Bacillus is obtained at 60° C. During the enzyme treatment, the pectinase produced by the microorganisms of the genus Bacillus effectively acts on protopectin, which is a pectin that bonds soybean cells together, so that the soybean cells can be efficiently separated from each other without destroying cell walls of the soybean.

The agitating operation should be performed to such a degree that the soybean cells are not destroyed. For example, it is preferred to select a mild agitating condition in which stirring wings are rotated in the first mixture at a speed of 20 rpm to 30 rpm. When such an agitating condition is selected, it is possible to allow the pectinase to uniformly act on the soybean cells, and gently separate the soybean cells from each other by the stirring wings. Therefore, the enzyme treatment can be smoothly performed. By this enzyme treatment, a slurry, in which single cells of the soybean are dispersed, is obtained.

Next, a heat treatment is performed on the slurry to inactivate the enzyme action of the pectinase. For example, it is preferred to heat the slurry at about 100° C. for 15 minutes.

Next, a second mixture is prepared by mixing the slurry with a powder obtained by processing a pulse other than the soybean. As the pulse other than the soybean, for example, it is possible to use pea, kidney bean or miscellaneous beans. As an example, a method of producing a pea powder is described below. First, a predetermined amount of pea is washed with water, and then soaked in water. For example, it is preferred to soak the pea in water at 14° C. for 16 hours or at 18° C. for 12 hours. Subsequently, a first heat treatment is performed on the pea. As the first heat treatment, it is preferred to simmer the pea for 30 minutes under atmospheric pressure, for example. After scum exuded from the pea by the first heat treatment is removed, a second heat treatment is performed. As the second heat treatment, it is preferred to heat the pea at 110° C. for 1 hour, for example. After the second heat treatment, the pea is dewatered, and crushed by use of a roll. By sifting the crushed pea through a sieve, a pea slurry is obtained. After water is added to the pea slurry, and a supernatant fluid of a resultant mixture is removed, a dewatering treatment is performed on a resultant product such that the water content is within a range of 63% to 68%. In addition, drying is performed to obtain the pea powder. As the drying method, it is preferred to select flash drying to be explained later or spray drying. The above-described method can also be applied to kidney bean and miscellaneous beans. It is preferred that the amount of the powder added to obtain the second mixture is substantially equal to the weight of the soybean measured before the soaking step.

A main purpose of adding the powder obtained by proceeding the pulse other than the soybean to the slurry is to regulate the slurry to a condition suitable for flash drying or spray drying in a drying step to be performed later. That is, soybean contains a large amount of lipid. Therefore, when the slurry containing the separated soybean cells is directly dried by the above drying method, oil constituents of the soybean cells prevent powder formation, so that a powder having uniform quality can not be obtained. In the present invention, it has been found that by adding the powder obtained by proceeding the pulse other than the soybean, in which the lipid content is low, to the slurry to improve the slurry condition, and then drying the improved slurry by the above drying method, the powder formation can be achieved while the separated soybean cells are maintained in good condition. Thus, the combination of the step of mixing the slurry with the powder obtained by processing the pulse other than the soybean to obtain the suitable slurry condition, and the step of drying the second mixture by the flash drying or spray drying method is important to provide the processed soybean powder having uniform quality without giving damages to the separated soybean cells dispersed in the slurry. Other conventional drying methods than the aforementioned drying methods, such as freeze-drying or vacuum drying, are not preferable because the separated soybean cells are destroyed in a pulverizing step performed after drying. Thus, when a slurry containing separated soybean cells is prepared, the above two steps are applicable to obtain a high-quality soybean powder from the slurry.

The second mixture thus obtained is dried by the flash drying or spray drying method. It is particularly preferable to select the flash drying method. In case of drying a material in a muddy or powdery state at damp to obtain a powder as a dried product, the flash drying method is defined as a method of quickly drying the material, which is characterized by supplying the material into a heated airflow having a rapid flow rate and carrying the material in the heated airflow along a direction parallel to the airflow. In general, an apparatus known as flash dryer is used for the flash drying method. In the present invention, it is preferred to perform the flash drying method at 120° C. for 5 seconds. When the spray drying method is selected, it is preferred to use a spray dryer.

According to the above-explained method, the processed soybean powder of the present invention can be produced. Optical microscope photographs of the processed soybean powder are shown in FIGS. 1 and 2. These photographs show that damages to the cell membranes and cell walls of the separated soybean cells are negligibly small, and the protein bodies and lipid bodies are maintained in good state in the interior of each of the separated soybean cells. Thus, the separated soybean cells of high quality are obtained.

By discontinuing the above-explained method immediately after the step of heating the slurry to inactivate the enzyme action of the pectinase, it is possible to obtain a slurry (puree), in which the soybean single cells are dispersed. This slurry can be used as a processed soybean liquid. This slurry has a noteworthy feature that the soybean cells are not destroyed even when the slurry is frozen and then thawed, or retort disinfection is performed on the slurry, for example, at 120° C. for 20 minutes.

When the processed soybean powder or liquid obtained by the present processing method is used as it is, it is possible to apply it as a food ingredient, diet food or a food for use in emergency. As previously described, the soybean is a highly nutritious food which is rich in vitamins and contains well-balanced protein, carbohydrate and lipid components. Therefore, it is expected the processed soybean powder and liquid are used as a relief aid in case of emergency or disasters, food ingredient for school-meal program or home cooked meal, and a space food in the future. In addition, since the present invention provides the method of processing the whole soybean without producing a waste, it will be a hopeful countermeasure for the predicted future food shortages. The processed soybean powder has an advantage that its weight is lighter than that of the processed soybean liquid, so that the soybean powder is convenient for transportation. The processed soybean powder is also convenient in that it can be easily turned into a liquid food on-site with the addition of water or the like.

It is also preferred to use a mixture of the processed soybean powder or liquid obtained by the present processing method and other food materials. In the past, the application range to other food materials of soybean has been limited because of the unpleasant smell peculiar to soybean in spite of its high nutritive value. However, since the processed soybean powder or liquid of the present invention has an improved digestion-absorption coefficient for the human body and the characteristic soybean smell all but disappears, it becomes possible to use the processed soybean powder or liquid together with various food materials.

For example, it is preferred to make foods using wheat flour such as breads, cakes and noodles, processed meat foods such as Hamburg steak and meat ball, mayonnaise, dressings, bean paste, cream, jam, curry, soup, ice cream, sherbet, or the like by using the processed soybean powder or liquid of the present invention. Consumers can ingest the nutritious constituents of soybean while enjoying various tastes and feelings of eating without sensing the soybean smell by eating the foods thus obtained.

EXAMPLES

The present invention is described below referring to its preferred embodiments.

Example 1

1.1 kg of dried soybean was washed with water, and then soaked in water for 12 hours. Without draining water used in the soaking step, the soybean was raised from water. Since the soybean absorbed water in the soaking step, the total weight of the soybean became 2.2 kg due to swelling. Subsequently, the soybean was steamed at 120° C. under 1.1 $kg/cm^2$ for 10 minutes by use of a pressure cooker. After the steamed soybean was cooled to 60° C., 2.2 kg of water used in the soaking step and 0.1 wt % of a pectinase (manufactured by NAGASE Biochemistry Company) produced by microorganisms of the genus Bacillus with respect to the weight of the dried soybean were added to the cooled soybean to obtain a first mixture.

The first mixture was held at 60° C. for 30 minutes while being agitated to achieve an enzyme treatment. Stirring wings were rotated at 30 rpm for the agitation. After the enzyme treatment, the degree of separation of the soybean cells from each other was observed by use of an optical microscope. The observation revealed that nearly complete separation of the soybean cells was achieved by this enzyme treatment. Therefore, performing the present enzyme treatment for 30 minutes is sufficient to achieve the purpose. In addition, it was observed that each of the separated soybean cells was maintained in good condition without receiving damages, and the dispersion state was favorable, too. Thus, a slurry (processed soybean liquid), in which single cells of the soybean are dispersed, was obtained. Analysis results of this slurry are shown in Table 1.

To inactivate the enzyme action of the pectinase, the slurry was heated at 100° C. for 15 minutes. Subsequently, 1.1 kg of a pea powder was added to the slurry to obtain a second mixture. The pea powder was prepared by the following method. First, pea was washed with water, and then soaked in water at 14° C. for 16 hours. Next, the pea was simmered for 30 minutes under atmospheric pressure. Scum exuded from the pea in the simmering step was removed, and then the pea was kept at 110° C. for 1 hour. After this heat treatment, the pea was dewatered, and crushed by use of a roll. By sifting the crushed pea through a sieve, a pea slurry was obtained. After water was added to the pea slurry, and a supernatant fluid of a resultant product was removed, a dewatering treatment was performed by use of a centrifugal dewatering machine such that the water content falls within a range of 63% to 68%. In addition, drying was performed by means of flash drying to obtain the pea powder.

Next, the second mixture was dried at 120° C. for 5 seconds by means of flash drying. As a result, a processed soybean powder of Example 1 according to the present invention was obtained. Optical microscope photographs of the obtained processed soybean powder are shown in FIGS. 1 and 2. Analysis results of the processed soybean powder are shown in Table 1.

TABLE 1

| | Slurry (Processed Soybean Liquid) | Processed Soybean Powder |
|---|---|---|
| pH value | 6.3 ± 0.3 | 6.3 ± 0.3 |
| water (in 100 g) | 82 g | 7.7 g |
| sugar (in 100 g) | 4.43 g | 46.2 g |
| lipid (in 100 g) | 3.9 g | 5.5 g |
| protein (in 100 g) | 5.94 g | 22.8 g |
| fiber (in 100 g) | 0.756 g | 16.2 g |
| ash content (in 100 g) | 1.6 g | 1.6 g |
| sodium (in 100 g) | 1.8 mg | 12.1 mg |
| energy (100 g) | 77.94 kcal | 326 kcal |
| heavy metals | Not detected | |
| arsenic | Not detected | |
| number of general germs | $1 \times 10^4$/g or less | |
| coliform bacteria | Negative | |
| Staphylococcus aureus | Negative | |

Comparative Example 1

5 kg of water was added to 1 kg of washed soybean, and the soybean was kept in water at room temperature for 12 hours. Then, an enzyme treatment was performed by adding 6 g of a pectinase produced by microorganisms of the genus Rhizopus to obtain a mixture, and holding the mixture at 28° C. for 8 hours while agitating the mixture. When the enzyme treatment was performed at 60° C., the enzyme action of the pectinase was inactivated, so that the enzyme treatment could not achieved within a predetermined time period. The degree of separation of the soybean cells from each other was observed by use of the optical microscope. The observation revealed that performing the enzyme treatment for at least 8 hours is needed to obtain nearly complete separation of the soybean cells.

Thus, a very long time period was needed to achieve the enzyme treatment in Comparative Example 1, and also the separation state of the soybean cells was not necessarily sufficient. Moreover, it is likely that miscellaneous germs would propagate if the enzyme treatment is performed at room temperature over an extended period of time.

Example 2

Bread was made by using the processed soybean powder obtained in Example 1 but not using yeast food under conditions shown in Tables 2 and 3. Table 2 shows a dough composition. Table 3 shows processing conditions for the dough and experimental results. FIG. 3 shows an optical microscope photograph of the bread of Example 2. This photograph was obtained by dissolving the obtained bread in water, and observing the solution with the optical microscope. The photograph reveals that each of the separated soybean cells is maintained in good condition even after baking. As Comparative Example 2, a bread was made by adding a predetermined amount of yeast food without using the processed soybean powder of Example 1 according to the conditions shown in Tables 2 and 3.

TABLE 2

| Com-<br>posi-<br>tion | Example 2 | | Comparative Example 2 | |
|---|---|---|---|---|
| | weight<br>(g) | weight ratio (%)<br>(weight of additive/<br>weight of flour) | weight (g) | weight ratio (%)<br>weight of additive/<br>weight of flour |
| wheat flour | 1600.0 | — | 1600.0 | — |
| yeast | 48.0 | 3.0 | 48.0 | 3.0 |
| yeast food | 0 | 0 | 1.6 | 0.1 |
| salt | 28.8 | 1.8 | 28.8 | 1.8 |
| sugar | 96.0 | 6.0 | 96.0 | 6.0 |
| oil and fat | 80.0 | 5.0 | 80.0 | 5.0 |
| pro-cessed soybean powder | 48.0 | 3.0 | 0 | 0 |
| water | 1104.0 | 69.0 | 1008.0 | 63.0 |
| total | 3004.8 | | 2862.4 | |

TABLE 3

| operation (weather: fine,<br>room temperature 26.5° C.) | Example 2 | Comparative<br>Example 2 |
|---|---|---|
| powder temperature | 25° C. | |
| water temperature | 15° C. | |
| mixing time | 13 minutes | |
| temperature at mixing | 29° C. | |
| time for fermentation (room temperature) | 60 minutes | |
| bench time | 15 minutes | |
| weight of each dough piece × the number of dough pieces | 240 g × 6 (total weight: 1440 g) | |
| holding time in temperature control apparatus (38° C.) | 45 minutes | |
| baking time<br>(set temperature for top side: 175° C.,<br>set temperature for bottom side: 195° C.) | 45 minutes | |
| weight of bread measured after the elapse of 1 hour from baking (first time) | 1310 g | 1292 g |
| weight of bread measured after the elapse of 1 hour from baking (second time) | 1308 g | 1292 g |
| average weight of bread | 1309 g | 1292 g |
| weight-change rate (average weight of bread/total weight of dough) | 90.9% | 89.7% |

In Example 2, 48 g of the processed soybean powder was used. In consideration of the amount of water absorbed in the processed soybean powder, the amount of water used in Example 2 was made 96 g (i.e., twice as large as the weight of the processed soybean powder) larger than that used in Comparative Example 2. Therefore, in Comparative Example 2, the ratio of the weight of water to the weight of wheat flour was 63%. In Example 2, the ratio of the weight of water to the weight of wheat flour was 69%. Thus, when adding 3% (i.e., 48 g) of the processed soybean powder with respect to the weight of the wheat flour, the added water content in the dough increased by 6%. The dough condition was favorable during the operation. It is believed that 6% of the added water (96 g) was absorbed into the interior of the soybean cells.

Characteristics of the bread were evaluated according a weight-change ratio calculated from bread weights measured before and after baking. As shown in Table 3, the weight-change ratio in Example 2 is 90.9%, and the weight-change ratio in Comparative Example 2 is 89.7%. The difference in the weight-change ratio, i.e., 1.2% (90.9–89.7), means that the amount of water lost during the baking step of Example 2 is smaller than that of Comparative Example 2. In other words, it shows that water retained in the soybean cells does not evaporate easily, so that yields can be improved.

In the bread-making industry, it is said that improving gelatinization of flour starch (transformation ratio from β flour starch to α flour starch) is important for making delicious bread, and increasing the water content of the dough and increasing the temperature at the center of the bread at the time of baking is useful for improving the gelatinization. When the processed soybean powder of the present invention is used, the effect of increasing the water content of the dough is obtained, as described above. In addition, since water retained in the interior of the soybean cells does not evaporate easily during the baking step, it acts as a heat transfer medium, so that the effect of increasing the temperature at the center of the bread is also obtained.

Water contained in bread is broadly divided into "bound water", which is combined with molecules of raw materials for bread and "free water", which is found between the molecules. However, the bread containing the processed soybean powder of the present invention further contains "intracellular water" (which is named "cell water" in the present specification.) retained in the interior of each of the separated soybean cells, in addition to the "bound water" and "free water". Therefore, it is possible to improve the moisture-retaining capability of the bread. The increase in water content retained in the bread of Example 2 shows that the bread of Example 2 is softer bread having a greater moisture-retaining capability than the bread of Comparative Example 2.

In Example 2, the bread contains 3% of the processed soybean powder of the present invention. In this case, it is estimated that about 5 single soybeans are contained in a slice (having a shape of about 15 cm×about 15 cm×about 1.5 cm) of the bread. When it is expressed in terms of the number of the soybean cells, the slice of the bread contains about 150 million cells. Since each of the separated soybean cells is in a capsule state having the intracellular water therein, an improved moisture-retaining capability of the bread is obtained without the unpleasant smell peculiar to soybean. Consequently, the bread of Example 2 can keep good taste over an extended time period and provide a soft feeling of eating.

In Example 2, 48 g of the processed soybean powder of the present invention and 98 g of water were added to 1600 g of the wheat flour, so that 3004.8 g of the dough was obtained. On the contrary, in Comparative Example 2, 2862.4 g of the dough was obtained by use of 1600 g of the wheat flour. Therefore, in Example 2, 142.4 g (3004.8–2862.4) of extra dough was obtained by use of the same amount of the wheat flour as Comparative Example 2. Thus, by adding a small amount of the processed soybean powder of the present invention, a large amount of extra dough exceeding the amount of the added processed soybean powder can be obtained from the same amount of the wheat flour as the conventional case. As a result, it is possible to provide the bread containing soybean as a nutritional supplement and having a soft feeling of eating to consumers at low prices.

In addition, the bread of the present invention can be made without using additives such as yeast food used in Comparative Example 2 or emulsifiers. Therefore, it is possible to provide a health food best suited to those consumers who give special attention to health.

Soybean contains a large amount of lysine, which is an essential amino acid for the human body. One previous approach to producing a lysine-contained bread was to pulverize soybean and mix the pulverized soybean in the bread. This approach, however, has never reached practical use because of the unpleasant smell characteristics to the soybean. Since the separated soybean cells of the processed soybean obtained by the present processing method are maintained in good condition without being destroyed, the soybean smell is all but eliminated. Therefore, deterioration of taste can be prevented when the processed soybean is mixed in the bread. Thus, the processed soybean of the present invention is suitable for making the lysine-containing bread having good taste.

Example 3

A noodle was made by use of the processed soybean powder obtained in Example 1. The amount of the processed soybean powder added was 5% of the total amount of raw material powder components including wheat flour. In Example 3, due to the addition of the processed soybean powder, the ratio of added water relative to the weight of the wheat flour was about 4% larger than a case of making the noodle without using the processed soybean powder (Comparative Example 3). The soybean smell of the conventional soybean powder was hardly perceived from the noodle containing the processed soybean powder when the noodle was prepared and tasted. The taste of the noodle of Example 3 was substantially same as that of Comparative Example 3. Further, the noodle was deep-fried so that it could be consumed as an instant noodle. Even when the noodle was deep-fried at a relatively low oil temperature, which was 10° C. lower than the oil temperature (140° C.) for frying the noodle of Comparative Example 3, substantially the same results as the conventional case were obtained. By lowering the oil temperature, the energy cost can be saved. In addition, since the amount of oil that adheres to the fried noodle is reduced, it is possible to provide a low-calorie instant noodle. Moreover, the water content of the noodle of Example 2 fried at the oil temperature of 130° C. was about 1.4% higher than that of the noodle of Comparative Example 3 fried at the oil temperature of 130° C.

As understood from the above results, by using the processed soybean powder of the present invention, the added water ratio was increased, and the noodle enhanced with nutritional constituents of soybean without the characteristic soybean smell was obtained by adding the processed soybean powder of the present invention.

Example 4

A Hamburg steak containing vegetables was made by use of the processed soybean powder obtained in Example 1. Table 4 shows the amounts of food ingredients used. After washing and boiling potato without removing the potato skin, the potato was roughly mashed. Shiitake was sliced after its stem was removed. After spinach was boiled and then chopped, water was removed from the spinach by squeezing it. Next, the food ingredients thus prepared were added to a chopped beef together with egg, bread crumbs, milk and the processed soybean powder. Salad oil and pepper were further added and a resultant mixture was kneaded well. The kneaded mixture was formed in a specified shape and, then, the shaped mixture was put on an oiled frying pan and fried over a slow flame for 3 to 4 minutes. Then, it was turned upside down, and further fried for 15 minutes with a lid placed on the frying pan to obtain the Hamburg steak containing vegetables. A Hamburg steak containing vegetables of Comparative Example 4 was made by substantially the same method as above except that the processed soybean powder was not used, and the amount of milk added was half the amount used in Example 4.

The soybean smell of the conventional soybean powder was hardly perceived from the Hamburg steak of Example 4 when it was prepared and tasted. In addition, the nutritional value of Hamburg steak was enhanced by adding the processed soybean powder. The amount of drips from the Hamburg steak of Example 4 was smaller than that from the Hamburg steak of Comparative Example 4. The Hamburg steak of Example 4 had a juicy and mild taste, and did not become hard even when it got cold.

TABLE 4

|  | Example 4 | Comparative Example 4 |
| --- | --- | --- |
| chopped beef | 400 g | 400 g |
| potato | 1 | 1 |
| spinach | 150 g | 150 g |
| shiitake | 4 | 4 |
| egg | 1 | 1 |
| bread crumbs | 12 g | 12 g |
| milk | 60 ml | 30 ml |
| onion | ½ | ½ |
| processed soybean powder | 40 g | 0 g |
| salad oil, salt, pepper, | proper quantity | proper quantity |

Example 5

A mayonnaise was made by use of the processed soybean powder obtained in Example 1. Table 5 shows the amounts of food ingredients used. Egg yolk was put in a dried bowl, and then pepper, salt and the processed soybean powder were added to the yolk. Then, they were mixed well by use of a whisk. While adding salad oil by successively dropping its few droplets onto the obtained mixture, the mixture was mixed by using the whisk. When the mixture became a creamy paste, vinegar was added and the mixture was further mixed well. The mixing operation was continued until a specified amount of the salad oil was fully added, to thereby obtain the mayonnaise containing the processed soybean powder. A mayonnaise of Comparative Example 5 was made by substantially the same method as above except that the processed soybean powder was not used, and the amount of vinegar added was about two-thirds the amount used in Example 5.

The soybean smell of the conventional soybean powder was hardly perceived from the mayonnaise of Example 5 when it was prepared and tasted. The mayonnaise of Example 5 was flavorous and mild, as compared with that of Comparative Example 5. Since the nutritional value of the mayonnaise is enhanced by adding the processed soybean powder and this mayonnaise is a health food containing fiber components of the soybean, it is expected to become an attractive food product for women who take interest in controlling their weight and figure.

TABLE 5

|  | Example 5 | Comparative Example 5 |
| --- | --- | --- |
| yolk of egg | 1 | 1 |
| vinegar | 23 ml | 15 ml |
| salt | about 2 g | about 2 g |
| processed soybean powder | 8.75 g | 0 g |
| salad oil | 100 ml | 100 ml |

Example 6

A French dressing was made by use of the processed soybean powder obtained in Example 1. Table 6 shows the amounts of food ingredients used. Pepper, salt and the processed soybean powder were put in a dried bowl. Wine vinegar was further put in the bowl, and a resultant mixture was mixed well to obtain a solution. Subsequently, while adding salad oil by successively dropping its few droplets into the obtained solution, the solution was mixed by use of a whisk. The mixing operation was continued until the color of the solution became milky-white and its viscosity became appropriate, to thereby obtain the French dressing containing the processed soybean powder. A French dressing of Comparative Example 6 was made by substantially the same method as above except that the processed soybean powder was not used, and the amount of wine vinegar added was about two-thirds the amount used in Example 6.

The soybean smell of the conventional soybean powder was hardly perceived from the French dressing of Example 5 when it was prepared and tasted. The French dressing of Example 6 was flavorous and mild, as compared with that of Comparative Example 6. In addition, the nutritional value of the French dressing was enhanced by adding the processed soybean powder.

TABLE 6

|  | Example 6 | Comparative Example 6 |
| --- | --- | --- |
| wine vinegar | 45 ml | 30 ml |
| salt | about 3 g | about 3 g |
| pepper | proper quantity | proper quantity |
| salad oil | 90 ml | 90 ml |
| processed soybean powder | 17.5 g | 0 g |

In conclusion, the method of processing soybean of the present invention and the processed soybean obtained by the present method have the following advantages.

1. Since the soybean cells are separated from each other by an enzyme treatment using a pectinase produced by microorganisms of the genus Bacillus, the smell characteristics to the soybean is all but eliminated. Therefore, the processed soybean can be utilized as a food ingredient in various fields.

2. Since "cell water" defined as water retained in the interior of each of the separated soybean cells does not evaporate easily, the processed soybean shows excellent moisture-retaining capability. Therefore, it is possible to improve the moisture-retaining capability of a food by using the processed soybean without using other additives, and consequently prevent deterioration of the food.

3. By using the pectinase produced by the microorganisms of the genus Bacillus, the enzyme treatment can be achieved in a very short time period, as compared to the conventional case. Therefore, the processed soybean can be produced at reduced production cost on an industrial scale, so that the scope of application of the processed soybean as the food ingredient will be widened.

4. From the viewpoint of biomass utilization, the processing method of the present invention can be applied to various foods and cereals. Therefore, it will play an important role in the solution of the global food shortages predicted to occur in the future.

What is claimed is:

1. A processed soybean preparation obtained by a method of processing soybean comprising the step of performing an enzyme treatment to the soybean in water with use of a pectinase produced by microorganisms of the genus Bacillus to decompose the soybean into single cells of the soybean, wherein said single cells of said soybean are dispersed in said processed soybean preparation, with damage to cell membranes or cell walls of said soybean cells being negligibly small, maintaining protein bodies and lipid bodies in an interior portion of said cells.

2. A bread containing said processed soybean preparation as set forth in claim 1.

3. A Hamburg steak containing said processed soybean preparation as set forth in claim 1.

4. A mayonaise containing said processed soybean preparation as set forth in claim 1.

5. A curry containing said processed soybean preparation as set forth in claim 1.

6. A noodle containing said processed soybean preparation as set forth in claim 1.

7. A dressing containing said processed soybean preparation as set forth in claim 1.

8. A soup containing said processed soybean preparation as set forth in claim 1.

9. A frozen confectionery containing said processed soybean preparation as set forth in claim 1.

* * * * *